(12) United States Patent
O'Foghludha

(10) Patent No.: US 6,547,816 B1
(45) Date of Patent: *Apr. 15, 2003

(54) FORMABLE INTEGRAL SOURCE MATERIAL FOR MEDICAL DEVICES

(75) Inventor: Fearghus O'Foghludha, Durham, NC (US)

(73) Assignee: CivaTech Corporation, Raleigh, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/506,611

(22) Filed: Feb. 18, 2000

Related U.S. Application Data
(60) Provisional application No. 60/143,296, filed on Jul. 12, 1999.

(51) Int. Cl.[7] ................................................ A61N 5/00
(52) U.S. Cl. ........................................... 623/1.15; 600/3
(58) Field of Search ........................... 600/1–9; 534/10; 424/1, 11, 53; 623/1.15

(56) References Cited

U.S. PATENT DOCUMENTS

| 6,152,869 A | * 11/2000 | Park et al. | .................... 600/3 |
| 6,231,495 B1 | * 5/2001 | Denk | ............................ 600/3 |

* cited by examiner

*Primary Examiner*—Michael H. Thaler
(74) *Attorney, Agent, or Firm*—Myers Bigel Sibley & Sajovec, PA

(57) ABSTRACT

The present invention provides an integral source material having at least one nuclide that is activatable by exposure to irradiation. The nuclide is a chemically bound constituent of a polymer making up the integral source material. Thus, the integral source material can be configured before activation into a medical device or component.

1 Claim, 2 Drawing Sheets

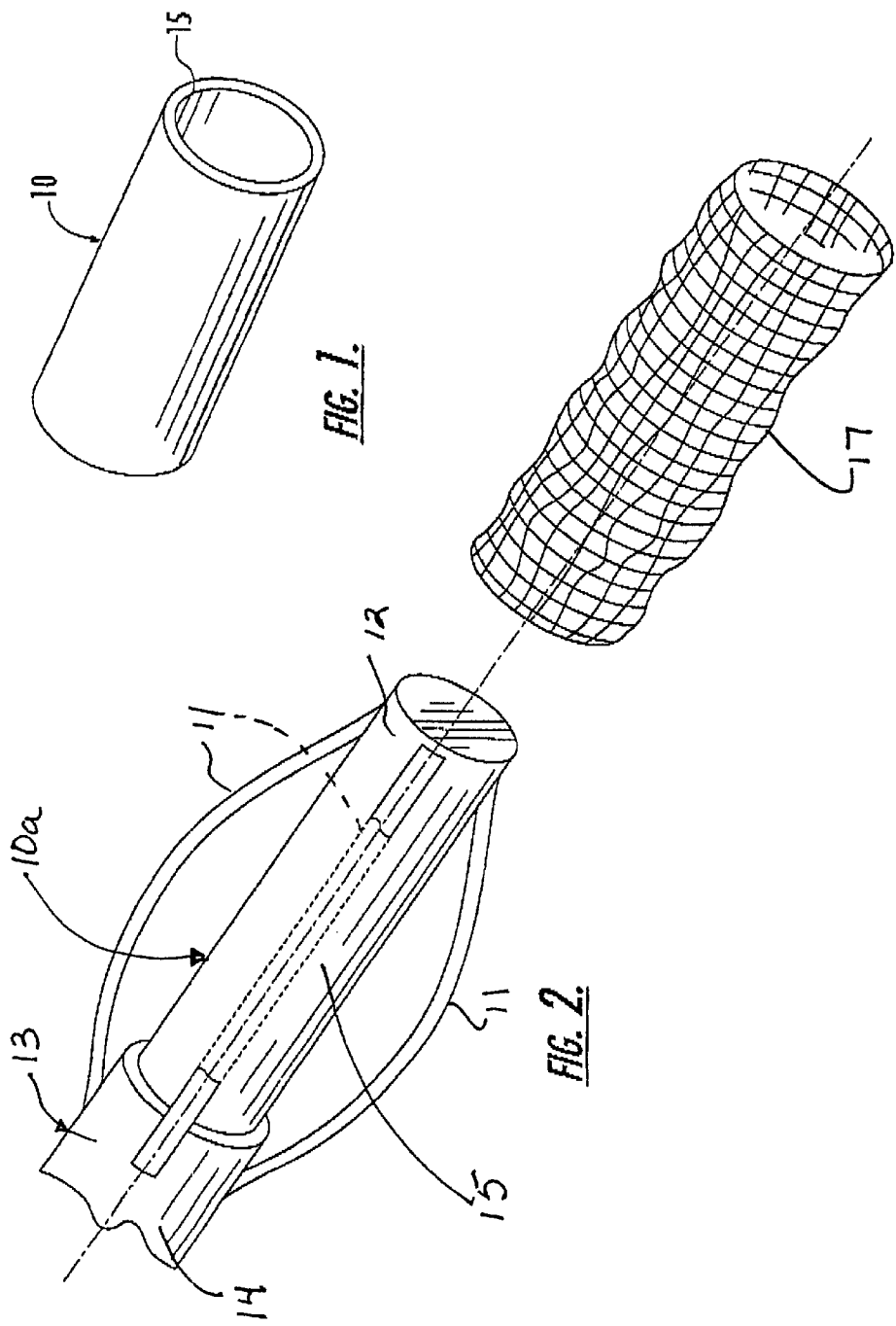

FORMABLE INTEGRAL SOURCE MATERIAL FOR MEDICAL DEVICES

RELATED APPLICATION

The present application claims a priority to U.S. Application Serial No. 60/143,296, filed Jul. 12, 1999, the disclosure of which is incorporated by reference herein in its entirety.

FIELD AND BACKGROUND OF THE INVENTION

The present invention relates to medical devices, and more particularly to the use of a formable source material having an activatable nuclide in medical devices.

Treatment of various medical conditions, notably cancer, with ionizing radiation is known. In one method of application, sources of gamma (γ) radiation, or more recently accelerators producing X-rays or electrons in the approximate energy range of 4 to 20 MeV, are used to direct intense collimated beams of radiation at tumors. To concentrate radiation effects in the tumor while sparing to the greatest possible extent the healthy tissues that usually surround it, multiple cross-firing beams intersecting in the tumor are often used. Because the origin of each beam is commonly at a relatively large distance, e.g., 1 meter, from the tumor, this external beam technique is sometimes referred to as tele- (for distant) therapy. In another method of application, referred to as brachy- (for short) therapy, radioactive sources, encapsulated if necessary to prevent escape of radioactive material into the tissues, are temporarily or permanently implanted in or are closely apposed to the tumor or other target tissue.

Various forms of brachytherapy include interstitial therapy where the sources, sometimes enclosed in needles, tubes or catheters, are physically inserted in the affected tissue; intracavitary therapy where source-containing applicators are introduced into naturally-occurring or artificial body cavities; treatment of certain shallow surface lesions by means of externally applied source-bearing containers often described as "molds"; intra- or endo-arterial irradiation where radioactive sources are inserted in the interior (lumen) of the affected blood vessels, and combinations or variations of these techniques. The type of source used depends on the particular field of application. Some sources emitting β-radiation only, as examples, can be used for intra-arterial brachytherapy because the targeted region of the arterial wall, which is in contact with the source, is heavily irradiated while tissues farther away than the β-ray range receive little or no dose; furthermore, intra-arterial lesions are usually thin, and their deeper regions can be adequately treated even with relatively non-penetrating β-particles. β-sources on the other hand are less suitable than γ-ray sources for irradiation of substantial tumor volumes because large numbers of β-sources must be precisely positioned to ensure that the tumor region is not underdosed if the sources are too far apart nor overdosed if they are too close together.

In interstitial brachytherapy of tumors, which are usually larger than intra-arterial lesions, a wide variety of sources and application methods has been used. The sources and methods of using them are generally familiar to those skilled in the art and include, but are not limited to, radium 226 in equilibrium with its decay products, radon 222, and more recently cobalt 60, cesium 137, gold 198, iridium 192, tantalum 182, iodine 125, palladium 103, and equilibrium mixtures of the β-emitters strontium 90 and yttrium 90, or yttrium 90 alone for specialized sites such as the pituitary gland. The choice of brachytherapy radionuclide will be within the capability of persons skilled in the art and will depend among other factors on the penetrating ability required of the radiation, the radiation emission rate, the half-life, the available activity, the tumor size, shape, location and cellular composition, on the clinical stage to which the tumor has progressed, on the patient's physical condition, on the experience and skill of the operator, on the availability and ability of assisting staff such as medical physicists and dosimetrists, and most particularly on whether the planned implant is to be temporary or permanent.

Specifically, intra-arterial brachytherapy can be used to prevent regrowth of tissue following the treatment of arteries for occlusive diseases, such as atherosclerosis. A commonly used method for treating atherosclerosis is Percutaneous Transluminal Coronary Angiopiasty (PTCA). PTCA includes insertion of a balloon catheter through an incision in the femoral artery near the groin, advancement of the balloon over the aortic arch, further advancement within the selected coronary artery, continuing until the balloon portion is placed across the narrowed (stenosed) region. The balloon is inflated, widening the stenosed region of the vessel.

After catheter withdrawal, significant vessel reclosure known as "restenosis" may develop and largely negate the dilation treatment. The reclosure may occur within hours or days of dilation, but more commonly occurs progressively, within six months of the angioplasty. One approach to dealing with restenosis utilizes stents, which are short tubular sections having a lumen therethrough, placed across the recently dilated vessel region. Stents can be either self-expanding or balloon-expandable. Stents are normally left in place indefinitely, though some versions may be designed for eventual removal. Stents, as any permanently implanted device, may cause long term problems. Because the stent constantly pushes radially outward against the vessel wall, the wall may be adversely affected over long periods, particularly in the regions adjoining the ends of the stent. The use of radiation, delivered to the target region either by external i.e., teletherapeutic means or by use of stents which have been made radioactive, has been suggested, for example by U.S. Pat. Nos. 5,059,166 to Fischell et al. and 5,199,939 to Dake et al. Suitable active stents can be made e.g. by immersing an inactive metal stent coated with a chelating agent in a solution of the desired radioactive material (see, for example, U.S. Pat. No. 5,871,436 to Eury), before insertion in the vascular lumen. Alternatively, the coated stent is immersed in a solution of an unactivated form of the desired nuclide, after which the stent, now bearing inactive material bonded to the metal by the chelator, is exposed to a suitable activating radiation and thereafter inserted in the artery. In yet another method (referred to as ion implantation) of manufacturing radioactive stents, ions of the inactive precursor of the desired radionuclide are driven into the stent surface by means of a high-energy accelerator, after which the stent is activated and inserted in the blood vessel. U.S. Pat. No. 5,873,811 to Wang et al. proposes using an adhesive which includes a radioactive material; the adhesive being applied to the vessel wall region to be treated.

These and other prior art stents have a number of limitations. A primary concern is the potential for leakage of the nuclide from the stent into the blood flowing in the vessel. Avoidance of the release of activated nuclide is often dependent on the quality of joining between the metal surfaces of the stent and the nuclide.

Therefore, an object of the present invention is to provide medical devices having activatable nuclides that are manufactured from materials that are both inexpensively available and easily configured into such devices, and are also permanently or temporarily insertable into the body.

Yet another object of the present invention is to provide medical devices that permit control of the radiation to various vessels and tumors while minimizing damage to tissue not to be treated.

Yet another object of the present invention is to provide devices whose manufacture and use is less hazardous than conventional radioactive devices. There will be less personnel exposure during manufacture because the device is formed before activation, and there is less chance of contamination during use because the radionuclides are integrally bound to the material of the device.

SUMMARY OF THE INVENTION

These objects and other objects and advantages are provided by the devices and methods of the present invention. Such devices and methods are useful in the administration of radiation in a wide variety of brachytherapy techniques including treatment of restenosis and of tumors. The present invention provides an integral source material having at least one nuclide that is activatable by exposure to ionizing radiation. The nuclide is a chemically bound constituent of a polymer making up the formable integral source material. Thus, the integral source material can be configured before activation into a medical device or component. Suitable medical devices that can be configured can include, but are not limited to the following: stents, seeds, catheters, irradiator tubes, applicators and molds, enclosures, shrouds, ribbons, rods, beads, needles, obturators, discs and the like, and various combinations thereof.

The activated nuclides can emit various types of radiation that can be used in brachytherapy. Primarily, beta or gamma radiation or a combination thereof is used. It is recognized by those skilled in the art that many secondary radiations accompany these principal emissions, for example, internal conversion, Auger and pair electrons internal and/or external bremsstrahlung, annihilation photons and characteristic x-rays.

BRIEF DESCRIPTION OF THE DRAWINGS

FIG. 1 is a perspective view of a typical stent of the present invention.

FIG. 2 is a perspective view of an embodiment of the present invention.

DETAILED DESCRIPTION OF THE INVENTION

Figure 3A:
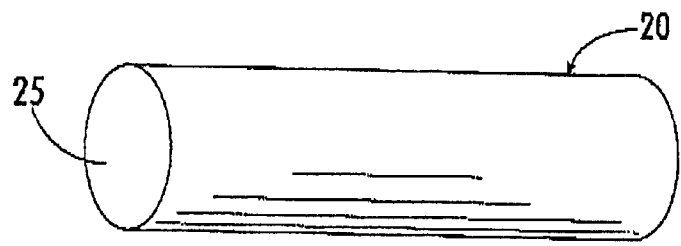
FIGS. 3a, 3b and 3c are side views of typical brachytherapy seeds of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As discussed above, in one aspect the present invention provides an integral source material having at least one nuclide that is activatable by exposure to ionizing radiation. The nuclide is a chemically bound constituent of a polymer making up the integral source material.

Any activatable nuclide that can be bound to a polymer is suitable. In general, the nuclide is preferably located in the backbone of the polymer, although side chain configurations are possible. Without being bound by any one theory, it is believed that the backbone configuration results in a more table integral source material. Typical weight fractions of nuclide in the olymer will be about 1 to 10 percent, although the selection of higher or lower weight fractions will be within the skill of one in the art.

Radiations usable for activation include neutrons and charged articles, for example, protons, deuterons, alpha particles, etc., the selection of which will be within the skill of one in the art. Once activated, the nuclides preferably emit β or γ radiation or x-rays or combinations thereof. The attainable activity can range from microcuries ($\mu$Ci) to millicuries (mCi). The activity reached depends on the nature and isotopic abundance of the target nuclide, its activation cross-section, the flux of activating radiation, the irradiation time, half-life and certain other properties.

As stated above, various nuclides that can become a chemically bound constituent of any polymer can be used. Suitable nuclides include, but are not limited to the following: Li, Na, C, F, Al, P, S, Cl, Ca, Ti, V, Cr, Mn, Fe, Co, Ni, Cu, Zn, Ge, Sr, Y, Zr, Mo, Tc, Rh, Pd, I, Cs, Ba, La, Ce, Eu, Gd, Re, Ir, Au, Hg, Pb, Bi, Po and Am. Combinations of such nuclides can be used, for example, a nuclide with a short half life may be used in combination with one having a longer half life. Suitable polymers include, but are not limited to the following: polypropylene, polyethylene terephthalate, nylon, acrylates, polyurethane, polyphenylene oxide blends, polyphenylsulfone, polysulfone, polyether sulfone, polyphenylene sulfide, phenyletheretherketone, polyetherimide, polyphenylmetallosiloxane, fluorine containing polyphosphazines and liquid crystal polymers.

The medical devices of the present invention can be utilized in various brachytherapy techniques including as examples angioplasty and treatment of malignant tissue within the brain, lung, esophagus, trachea, oropharynx, uterus, uterine cervix, biliary ductal system, colon or rectum, the gynecological system, prostate, head and neck, including the pituitary gland. The radiation can be applied internally, or externally in the case of surface lesions, while minimizing exposure of healthy tissue and of health care providers.

Suitable medical devices that can be configured can include, but are not limited to the following: stents, seeds, catheters, irradiator tubes, applicators and molds, enclosures, shrouds, ribbons, rods, beads, needles, obturators, discs, and the like, and various combinations thereof. Devices of almost any shape can be fabricated while the polymer and its chemically bound nuclide are inert i.e., non-activated. Importantly, such devices can be formed without radiation hazard using existing polymer processing techniques including the use of plasticizers to modify physical properties such as flexibility. Moreover, such devices may be fabricated to take into account the volume (or area in the case of surface lesions) of the tissue to be irradiated, its location, and the depth of penetration needed.

Intra-arterial stent devices and components produced according to the present invention are generally thin-walled cylindrical structures whose rigid or flexible outer walls (or covering layers affixed to those walls) are formed from a base polymer matrix having at least one activatable target nuclide as a tightly-bound chemical constituent thereof. The stents, after activation, can be placed in blood vessels in order to treat, or aid in preventing, the re-stenosis that often follows initially successful angioplastic dilation.

A device of the present invention configured accordingly to the present invention and taking the form of a stent 10 is shown in FIG. 1.

In the example of a radioactive stent device 10a shown in FIG. 2, one end of each of several flexible members 11 (three of which are shown), preferably composed of a polymer rather than a metallic material, are attached at the distal end 12 by a flexible introducing cable 13 in the form of a steerable catheter (which may if desired be furnished with a balloon), the proximal end 14 of which is outside the patient's body. The other end of each flexible member is attached to the tip of a central wire 15 coaxial with and sliding within the introducer proper 13. Medical staff can retract or advance the tip of the central member by means of an external control, retraction causing a given point on a flexible member to move radially outward and advancement causing a collapse inward. A loosely-woven tubular mesh 17 composed of the integral source material of the invention is attached to the cage-like assembly of flexible members. On operation of the retraction mechanism, the mesh 17 is expanded outwards so that it bears against the vessel wall from which, if desired, it can be slightly separated by a very thin layer of balloon material (not shown). The mesh, the flexibility of whose constituent threads can, if desired, be modified during the manufacturing process by means of plasticizers, can be activated separately from the rest of the device by exposure to a suitable source of radiation, and then attached to the expanding/collapsing cage. Alternatively, the entire end of the device can be made detachable; this permits the mesh to be attached to the expanding mechanism in complete safety while the mesh is still inactive. The entire end with attached mesh is then exposed to the activating radiation and when suitably active is re-connected, an operation that can be carried out more quickly and thus more safely than the more complex one of mounting an already active mesh segment to the flexible members.

In one embodiment of the invention the mesh 17 is fabricated from threads or strands of the base polymer polyarylene ether phosphine oxide which contains as target substance (i.e. activatable nuclide) about 9.7% by weight of phosphorus 31, whose isotopic abundance is 100%. On exposure to thermal neutron radiation the initially inactive phosphorus 31 is activated and becomes phosphorus 32, a pure β-emitter with maximum energy of about 1.72 MeV and half life of about 14 days; none of the other constituents of the base polymer is activated. The phosphorus is substantially chemically contained in the mesh material. Because of the high concentration of phosphorus in the base polymer the material can if desired be activated to a saturation specific activity of about 10 mCi per gram of polymer by exposure to thermal neutron fluence rates that are readily produced by typical nuclear reactors. Charged-particle activating beams from accelerators may be used when the desired radionuclide cannot easily be produced (as $^{32}$P can) by neutron capture.

Figure 3B:
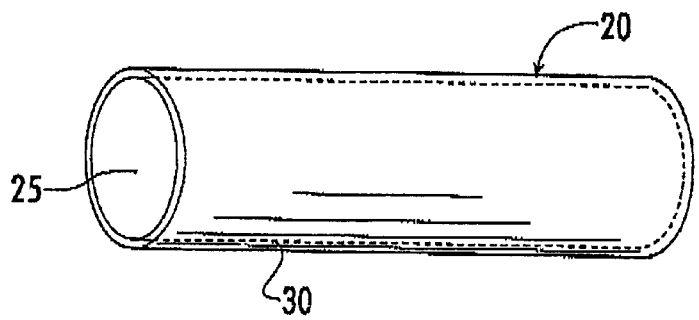
Figure 3C:
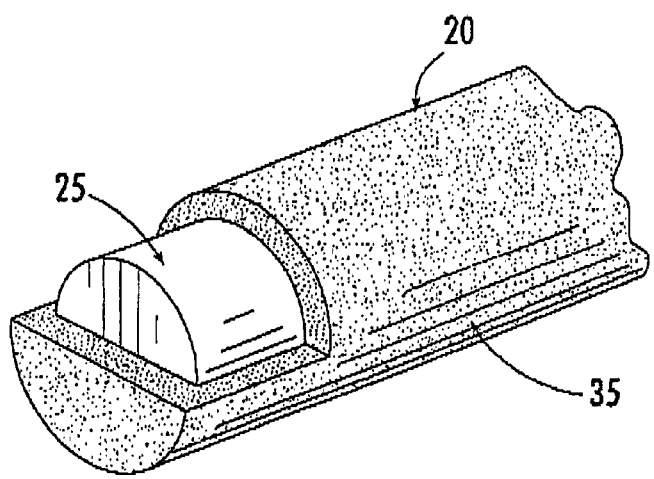

Another exemplary device of the present invention takes the form of a brachytherapy seed 20 shown in FIGS. 3a, 3b and 3c. Such seeds, suitably placed in and around tumors, can deliver high doses to the tumor without unduly adverse effects on neighboring healthy tissues. In one embodiment as shown in FIG. 3a, the seed 20 is solid throughout and is essentially formed from the base matrix polymer 25 with activatable nuclide and encapsulation to prevent escape of radioactive material is essentially performed by the invention material itself, which can shed radioactivity only in the form of swarf produced by abrasion. In another embodiment as shown in FIG. 3b, the seed 20 has a core of the base matrix polymer 25 with activatable nuclide and an outer layer or sheath 30 of an inert polymer material the same or different from the polymer of the base matrix polymer. Stated otherwise, the active integral source material is encapsulated within an inactive polymer. In yet another embodiment shown in FIG. 3c, the seed 20 has a core of the base matrix polymer 25 and an outer layer 30 or sheath of inactive polymer wherein the polymer contains additional screening material 35. Thus, the outer layer augments the self-encapsulating role of the invention material and simultaneously filters the photon output and screens out undesired β-particles. Seeds are preferably nylon or polyethylene and the target nuclides are selected from the group consisting of possible precursors, depending on the activation route, of the desired radioactive species.

Such seeds can be introduced into the tumor through a variety of ways, e.g., via flexible catheter, cannula with trocar point, etc., the selection and use of which will be within the skill of one in the art. Exemplary other seeds are discussed in, for example, U.S. Pat. No. 5,405,309 to Carden Jr., U.S. Pat. No. 5,354,257 to Roubin, U.S. Pat. No. 5,342,283 to Good, U.S. Pat. No. 4,891,165 to Suthanthirian, U.S. Pat. No. 4,702,228 to Russell et al., U.S. Pat. No. 4,323,055 to Kubiatowicz and U.S. Pat. No. 3,351,049 to Lawrence, the disclosures of which are incorporated herein by reference in their entirety.

In accordance with well-known brachytherapy techniques such seeds, often arranged in linear strands or in more complex arrays, can also be inserted in channels or recesses in obturators conformed to fit closely into body cavities such as for example the rectum, vaginal cavity, uterine cervix, nasal cavity, auditory canal, maxillary antrum, etc., with the objective of irradiating lesions located at or just beneath the lining of the cavity into which the obturator is inserted. Placement of seeds on the surface of a mold or plaque is also possible in order to treat lesions located at or immediately below the surface area to which the radiant sources are mounted, usually on a stand-off mold.

The above-described stents and seeds are merely exemplary of the type of devices that can be fabricated. The formability of the source material is highly advantageous since the material can be machined (drilled, milled, turned, sawn, etc.), molded, tested and the like. The selection of the fabrication method (which can include micromachining with laser radiation) will be within the skill of one in the art, to make a myriad of devices. Other types of devices include tubing designed to irradiate liquids as they pass through it, for example in blood irradiators. Although such tubing can be made by extruding already active material, this method is hazardous and unavoidably contaminates the forming devices. The integral source of the present invention can be used to extrude inert forms of subsequently activated polymers; this method is safe and eliminates radiation contamination of the forming equipment.

Using the integral source material of the invention, the above interstitial, intercavitary, and surface procedures can be carried out with the advantage, among others, that the radiation emission need no longer be confined to discrete seed, tube or needle locations but can be arranged, because of the formability of the source material, in spatial patterns whose activity can vary continuously over the treated area; an additional advantage is that the flexibility of the invention source materials enables them to be used in the form of long uniformly-activated flexible strands which can be bent or curved at will, rather than in the necessarily straight-line configurations of a source composed of rigid segments. The continuous-strand source, in addition to its flexibility, has the advantage that the nested surfaces surrounding the source, over any one of which the radiation intensity is constant (i.e., the isodose surfaces) do not show depressions or pinches, as do the surfaces surrounding strands made up of multiple seeds interrupted by gaps, considerably facilitating the specification, calculation and measurement of the delivered dose. The typically lower mass density and atomic number of the typical invention seeds also diminishes the known phenomenon of flux anisotropy, that is the occurrence of smaller fluxes opposite the ends of a seed relative to the fluxes observed laterally, a troublesome dosimetric complication that is exacerbated when multiple seeds are used, e.g. as an array of line sources, each line composed of seeds having inactive gaps between them. The single-seed anisotropy is caused in part by the different degrees of intra-source absorption as radiation seeks to escape along the seed axis or in a direction perpendicular to that axis; anisotropy is further exaggerated when, as in most presently available seeds, a metal encapsulation is used, usually thicker at the ends of the seed than in its lateral wall and usually composed of higher density and higher atomic number material than that used in the seeds of the invention.

As an example, it is known that a radial intensity pattern can be produced that is approximately but not totally uniform over the plane of, e.g., a roughly circular lesion, when the lesion is separated by a calculable distance from a second plane, approximately parallel to the first in which radiating material is arranged in the form of a ring of seeds, short tubes, or other discrete sources. Because the ring consists of several discrete sources rather than a single continuous one, as field calculations assume, the intensity distribution in the plane of the lesion is never perfectly uniform. Use of continuous strand sources, with no activity gaps, minimizes this difficulty. In addition, when the radius of the lesion is large, it becomes necessary to add a second ring and in extreme cases a point-like central source to combat the fall of intensity at the center of the arrangement. Using the formable materials of the invention, a compensatory activity gradient can be produced by machining a block of inert, i.e., not yet activated source material, into the form of a lens, thereby adjusting the mass and therefore the activity immediately above a specific point of the lesion in such a way that, in combination with radiation emitted from all other regions, the doses delivered at all points in the plane of the lesion are the same or very nearly so.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An integral source material having at least one P nuclide that is activatable by exposure to radiation, the P nuclide is a chemically bound constituent of a polyarylene ether phosphine oxide polymer of the integral source material, wherein the integral source material is configured before activation to provide a radioactive stent.

* * * * *

UNITED STATES PATENT AND TRADEMARK OFFICE
CERTIFICATE OF CORRECTION

PATENT NO.    : 6,547,816 B1
DATED         : April 15, 2003
INVENTOR(S)   : O'Foghludha It is certified that error appears in the above-identified patent and that said Letters Patent is hereby corrected as shown below:

<u>Title page,</u>
Item [56], U.S. PATENT DOCUMENTS, should include:
-- 3,351,049   11/67   Lawrence
4,323,055      4/82    Kubiatowicz
4,510,924      4/85    Gray
4,702,228      10/87   Russell, Jr. et al.
4,754,745      7/88    Horowitz
4,763,642      8/88    Horowitz
4,891,165      1/90    Suthanthiran
5,199,939      4/93    Dake et al.
5,342,283      8/94    Good
5,354,257      10/94   Roubin et al.
5,405,309      4/95    Carden, Jr.
5,683,345      11/97   Waksman et al.
5,713,828      2/98    Coniglione
5,782,740      7/98    Schneiderman
5,840,008      11/98   Klein et al.
5,840,009      11/98   Fischell et al.
5,863,284      1/99    Klein
5,871,436      2/99    Eury
5,873,811      2/99    Wang et al.
5,894,133      4/99    Armini
5,899,882      5/99    Waksman et al.
5,916,143      6/99    Apple et al. --

Signed and Sealed this

Twenty-third Day of December, 2003

JAMES E. ROGAN
*Director of the United States Patent and Trademark Office*